(12) United States Patent
Stopek

(10) Patent No.: US 10,603,044 B2
(45) Date of Patent: Mar. 31, 2020

(54) SURGICAL INSTRUMENTS FOR USE WITH DIAGNOSTIC SCANNING DEVICES

(75) Inventor: Joshua Benjamin Stopek, Guilford, CT (US)

(73) Assignee: Covidien LP, Mansfield, MA (US)

( * ) Notice: Subject to any disclaimer, the term of this patent is extended or adjusted under 35 U.S.C. 154(b) by 549 days.

(21) Appl. No.: 13/440,223

(22) Filed: Apr. 5, 2012

(65) Prior Publication Data

US 2012/0316424 A1    Dec. 13, 2012

Related U.S. Application Data

(60) Provisional application No. 61/479,569, filed on Apr. 27, 2011.

(51) Int. Cl.

| | | |
|---|---|---|
| *A61B 17/068* | (2006.01) | |
| *A61B 17/128* | (2006.01) | |
| *A61B 17/072* | (2006.01) | |
| *A61B 17/115* | (2006.01) | |
| *A61B 17/00* | (2006.01) | |

(Continued)

(52) U.S. Cl.
CPC ........ *A61B 17/1285* (2013.01); *A61B 17/068* (2013.01); *A61B 17/072* (2013.01); *A61B 17/07207* (2013.01); *A61B 17/1155* (2013.01); *A61B 5/055* (2013.01); *A61B 6/032* (2013.01); *A61B 6/12* (2013.01); *A61B 2017/0092* (2013.01); *A61B 2017/00911* (2013.01); *A61B 2090/374* (2016.02); *A61B 2090/376* (2016.02); *A61B 2090/3762* (2016.02); *A61B 2562/182* (2013.01)

(58) Field of Classification Search
CPC .......... A61B 17/0684; A61B 17/07207; A61B 17/320016; A61B 17/0401; A61B 17/0487; A61B 17/064; A61B 17/072; A61B 17/07292; A61B 2017/0417; A61B 2017/07214
USPC .............. 606/139, 153, 155, 219; 227/179.1, 227/180.1, 19, 176.1, 175.1; 600/140, 600/142; 411/444, 457, 920
See application file for complete search history.

(56) References Cited

U.S. PATENT DOCUMENTS

| | | |
|---|---|---|
| 2,821,500 A | 1/1958 | Jackson et al. |
| 4,619,391 A | 10/1986 | Sharkany et al. |

(Continued)

FOREIGN PATENT DOCUMENTS

| | | |
|---|---|---|
| DE | 19858578 | 6/2000 |
| EP | 0 686 374 A2 | 12/1995 |

(Continued)

OTHER PUBLICATIONS

European Office Action dated Feb. 10, 2017, issued in EP Application No. 12165629.

*Primary Examiner* — Elmer M Chao

(57) ABSTRACT

A surgical instrument for treating tissue during use of a diagnostic scanning device. The surgical instrument includes a housing, an actuating mechanism and an end effector assembly. The actuating mechanism is configured to activate the end effector assembly to treat tissue. At least a portion of the end effector is made of a material that is compatible with the diagnostic scanning device and allows a user to insert and activate the end effector to treat tissue at a surgical site within a patient while the surgical site is monitored during diagnostic scanning device.

20 Claims, 5 Drawing Sheets

(51) Int. Cl.
*A61B 6/03* (2006.01)
*A61B 5/055* (2006.01)
*A61B 6/12* (2006.01)
*A61B 90/00* (2016.01)

(56) References Cited

U.S. PATENT DOCUMENTS

| | | | |
|---|---|---|---|
| 4,619,891 | A | 10/1986 | Takahashi |
| 5,062,846 | A | 11/1991 | Oh et al. |
| 5,080,665 | A | 1/1992 | Jarrett et al. |
| 5,324,307 | A | 6/1994 | Jarrett et al. |
| 5,514,148 | A | 5/1996 | Smith, III |
| 5,662,662 | A | 9/1997 | Bishop et al. |
| 5,805,312 | A | 9/1998 | Ozawa et al. |
| 5,829,662 | A | 11/1998 | Allen et al. |
| 5,855,312 | A | 1/1999 | Toledano |
| 6,086,586 | A * | 7/2000 | Hooven ............. 606/50 |
| 6,264,086 | B1 * | 7/2001 | McGuckin, Jr. ........... 227/180.1 |
| 6,338,737 | B1 | 1/2002 | Toledano |
| 6,423,079 | B1 * | 7/2002 | Blake, III ............. 606/143 |
| 6,607,542 | B1 | 8/2003 | Wild |
| 8,128,643 | B2 * | 3/2012 | Aranyi et al. ............. 606/143 |
| 2004/0092960 | A1 | 5/2004 | Abrams et al. |
| 2004/0254608 | A1 | 12/2004 | Huitema et al. |
| 2005/0051597 | A1 | 3/2005 | Toledano |
| 2005/0251177 | A1 * | 11/2005 | Saadat et al. .............. 606/153 |
| 2006/0052824 | A1 | 3/2006 | Ransick et al. |
| 2007/0135711 | A1 * | 6/2007 | Chernomorsky et al. .... 600/431 |
| 2008/0021500 | A1 | 1/2008 | Shifrin et al. |
| 2008/0048002 | A1 | 2/2008 | Smith et al. |
| 2008/0306333 | A1 | 12/2008 | Chin |
| 2009/0062799 | A1 | 3/2009 | Holsten et al. |
| 2009/0114701 | A1 * | 5/2009 | Zemlok et al. ............ 227/176.1 |
| 2009/0236401 | A1 | 9/2009 | Cole et al. |
| 2011/0098531 | A1 * | 4/2011 | To ................. A61B 17/1671 600/114 |

FOREIGN PATENT DOCUMENTS

| | | |
|---|---|---|
| EP | 0 686 374 A3 | 8/1996 |
| EP | 0546767 | 9/1998 |
| EP | 0 686 374 B1 | 10/2002 |
| EP | 1857056 | 11/2007 |
| EP | 1 322 214 B1 | 3/2008 |
| WO | WO 02/24058 A2 | 3/2002 |
| WO | WO 2007/038715 A1 | 4/2007 |
| WO | WO 2008/106086 A1 | 9/2008 |
| WO | 2010123825 A1 | 10/2010 |

* cited by examiner

SURGICAL INSTRUMENTS FOR USE WITH DIAGNOSTIC SCANNING DEVICES

The present application claims the benefit of and priority to U.S. Provisional Application Ser. No. 61/479,569, filed on Apr. 27, 2011, the entire contents of which are incorporated herein by reference.

BACKGROUND

Technical Field

The present disclosure relates to surgical instruments. More particularly, the present disclosure relates to surgical instruments that are compatible for use during diagnostic testing, for example, magnetic resonance imaging, computed tomography scanning and X-ray scanning.

Description of Related Art

Diagnostic scanning devices are commonly used by physicians and/or surgeons to diagnose diseases in patients or view the operative site during a surgical procedure. An example of a diagnostic scanning device is a magnetic resonance imaging (MRI) scanner. An MRI scanner uses high-powered magnets to render images of an internal body cavity of a patient. It is primarily used in medical imaging to demonstrate pathological or other physiological alterations of living tissue. Another example of a diagnostic scanning device is a computed tomography (CT) scanner, which uses X-rays (another diagnostic test) to acquire X-ray images, making it a beneficial tool for examining tissue composed of elements of a relatively higher atomic number than the tissue surrounding them, such as bone and calcifications within the body.

Both MRI and CT scanners are non-invasive and can generate multiple two-dimensional cross-sections (slices) of tissue and three-dimensional reconstructions. By variation of scanning parameters, tissue contrast can be altered and enhanced in various ways to detect different features.

While diagnostic scanning devices are useful and helpful, such devices, with regard to MRI scanners, have an effect on ferromagnetic foreign bodies or metallic implants (e.g. surgical prostheses and aneurysm clips) due to their interaction with magnetic and radiofrequency fields, which can lead to a disruption or compromise of image and/or data quality.

As minimally invasive surgery progresses and the use of intra-operative imaging are further integrated into the operating room, the need for surgical instruments that are compatible with diagnostic testing and related scanning devices exists. It is increasingly necessary for a surgeon and/or clinician to view an operative site, with a diagnostic scanning device, following insertion of a surgical instrument within a body cavity of a patient. Current surgical instruments are composed of a variety of metallic and polymer components, some of which are not compatible with a diagnostic scanning device, such as a MRI scanner. These types of components may disrupt or compromise image and data quality of a diagnostic test, and interfere with the surgeon and/or clinicians use of the surgical instrument.

SUMMARY

The present disclosure relates to a surgical instrument for treating tissue during use with a diagnostic scanning device. The surgical instrument includes a housing, an actuating mechanism and an end effector assembly. The actuating mechanism is configured to activate the end effector assembly to treat tissue. At least a portion of the end effector assembly is constructed from a material that is compatible with the diagnostic scanning device and that allows a user to insert and activate the end effector to thereby treat tissue at a surgical site within a patient while the surgical site is monitored during diagnostic testing. The end effector may be clear, transparent, translucent or radio-translucent to the scanning device.

In some embodiments of the present disclosure, the diagnostic scanning device may be a magnetic resonance imaging device, a computed axial tomography scanning device or an X-ray scanning device. In some embodiments, the compatible material may be a non-ferrous metal and/or a non-metallic material such that at least a portion of the surgical instrument is radio-translucent during diagnostic testing.

The actuating mechanism in some embodiments includes a handle assembly that includes a fixed handle and a moveable handle. The handle assembly may be operatively coupled to the end effector assembly, wherein actuation of the handle assembly activates the end effector assembly to treat tissue.

In some embodiments of the present disclosure, the surgical instrument may be a surgical stapling device. The end effector assembly of the surgical stapling device may include a stapling cartridge and an anvil assembly. In some embodiments, every component of the stapling cartridge and the anvil assembly may be composed of material that is compatible with a diagnostic scanning device to thereby staple tissue at the surgical site within a patient while the surgical site is monitored during diagnostic testing.

During use, preferably the stapling cartridge and the anvil assembly are approximated towards each other to clamp tissue therebetween and to enable the clinching of staples in tissue upon expulsion of the staples at the surgical site within a patient while the surgical site is monitored during diagnostic testing.

In other embodiments, the surgical instrument is a surgical clip applier. The surgical clip applier may include a handle portion, a body extending distally from the handle portion and defining a longitudinal axis, a plurality of surgical clips disposed within the body, and a jaw assembly mounted adjacent a distal end portion of the body. Each of these components may be entirely composed of a material that is compatible with a diagnostic scanning device to thereby clip tissue at the surgical site within a patient while the surgical site is monitored during diagnostic testing.

In another aspect of the present disclosure, a method of treating tissue during use of a diagnostic scanning device is disclosed. The method initially includes the step of providing a surgical instrument that has a housing and an actuating mechanism configured to activate an end effector assembly. At least a portion of the end effector assembly is constructed from a material that is compatible with the diagnostic scanning device and that allows a user to insert and activate the end effector to thereby treat tissue at a surgical site within a patient while the surgical site is monitored during diagnostic testing. The end effector may be clear, transparent, translucent and/or radio-translucent to the scanning device. The end effector of the surgical instrument is inserted into the surgical site and the surgical site is scanned and monitored with the diagnostic scanning device. The surgical site is treated with the end effector of the surgical instrument while the surgical site is being scanned and monitored.

BRIEF DESCRIPTION OF THE DRAWINGS

The present disclosure will be more fully appreciated as the same becomes better understood from the following detailed description when considered in connection with the following drawings, in which.

DETAILED DESCRIPTION

Figure 1:
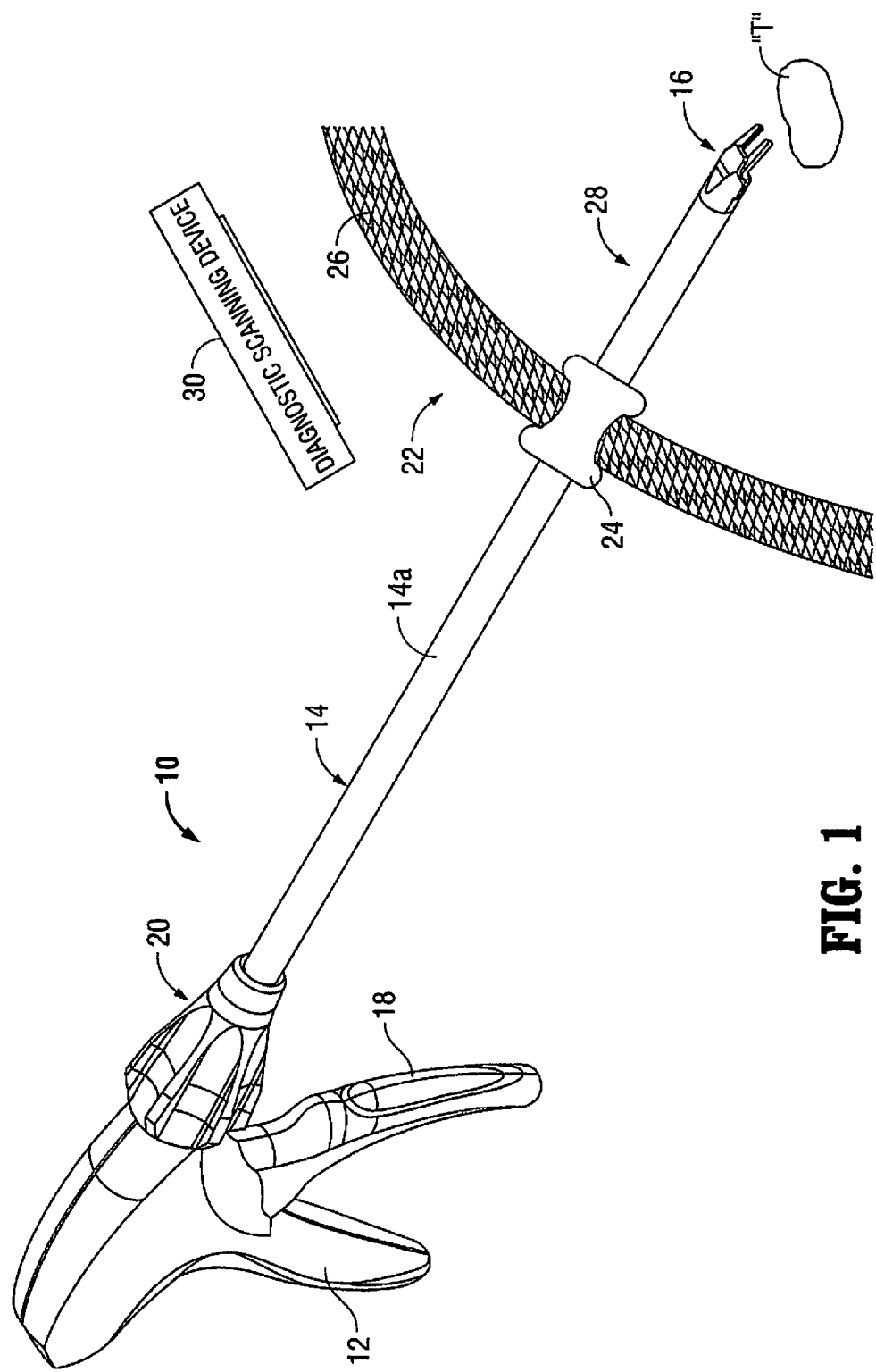
FIG. 1 is a perspective view of an exemplary endoscopic surgical clip applier including components being compatible with diagnostic scanning devices, in accordance with an embodiment of the present disclosure.

Embodiments of the presently-disclosed surgical instruments and their components are described in detail with reference to the drawings wherein like reference numerals identify similar or identical elements. As shown in the drawings and described throughout the following description, as is traditional when referring to relative positioning on a surgical instrument, the term "proximal" refers to the end of the device which is closer to the user and the term "distal" refers to the end of the device which is further away from the user.

In general, the present disclosure relates to single-use and/or re-useable surgical instruments that are partially or entirely composed of materials that are compatible during use of diagnostic scanning devices such as MRI scanners. Some of these surgical instrument materials include polymers, plastics, and/or non-ferrous metals, such as titanium or aluminum.

A novel aspect according to the present disclosure is that any suitable surgical instrument may be selected and configured to comprise a material that is compatible with diagnostic scanning devices. Some examples of suitable instruments include open instruments, endoscopic instruments, laparoscopic instruments, natural orifice transluminal endoscopic surgery (NOTES) enabling instruments, and single incision surgical procedure, e.g., SILS™, enabling instruments. Some specific examples of suitable instruments that may be used in accordance with the present disclosure are ENDO CLIP™ appliers, TA™ staplers, ENDO-GIA™ staplers, EEA™ staplers, surgical instruments used with SILS™ ports, all of these instruments are commercially available and offered by Covidien AG.

As discussed above, an example of a diagnostic scanning device is an MRI scanning device. Since an MRI scanning device uses high powered magnets, it is desirable that non-ferrous metallic components are utilized at or near an MRI scanning device. During an open or a laparoscopic surgical procedure, it may be necessary or desirable to view and/or record the operative site with a scanning device, such as an MRI or a CT scanner. Accordingly, utilization of non-ferrous metallic components and/or MRI or CT friendly components for the surgical instruments would be advantageous.

Thus, in order to avoid any side effects, e.g. image disruption, during the MRI scanning, a surgical instrument that is constructed of only non-ferrous metallic components and/or MRI/CT friendly components will allow a surgeon and/or user to perform and view a surgical procedure while the MRI scanning is taking place. Exemplary embodiments utilizing the aspects of compatible material will be described hereinbelow. Other suitable materials that may be utilized with the instruments that will not interfere with MRI scanning include titanium, copolymers, plastics and/or carbon fiber.

In other embodiments of the present disclosure, any suitable surgical instrument may be selected and configured to comprise a radio-translucent material. In this manner, the surgical instrument may not include any or a minimum number of metallic structures/components such that during a diagnostic test (e.g., a CT or MRI scan) or surgical procedure conducted under CT or MRI scanning, the diagnostic scanning device is able to capture the images that are disposed "behind" the device. That is, the surgical instrument may appear to be "translucent," "radio-translucent," "invisible," or "clear" in a diagnostic scanning device image result. For example, the components of this type of surgical instrument may be made of clear, translucent or radio-translucent plastic. In this manner, the radio-translucent material will permit X-rays to penetrate and pass through the surgical instrument.

Referring now to FIG. 1, a surgical instrument according to the present disclosure in the form of a surgical clip applier 10 is shown, and generally includes a handle assembly 12 and an endoscopic portion 14 having an elongated tubular member 14a that extends distally from the handle assembly 12. The handle assembly 12 is made from a thermoplastic material and the elongated tubular member 14a is made from a biocompatible material. In one embodiment, the endoscopic portion 14 may be constructed from a non-ferrous metallic material, for example, a titanium material or alloy. Endoscopic portion 14 includes an end effector in the form of a pair of jaws 16 mounted on the distal end of the tubular member 14a. The jaws 16 are actuated by a trigger 18 of handle assembly 12. The endoscopic portion 14 also has a knob 20 rotatably mounted on a distal end of the handle assembly 12 and is connected to the elongated tubular member 14a to provide a three hundred sixty degree (360°) rotation of the elongated tubular member 14a.

During a diagnostic test or surgical procedure, as shown in FIG. 1, a diagnostic scanning device 30 (e.g., an MRI scanner) is used to scan and render an image at a surgical site 22. An access port 24 is positioned within a tissue or body layer 26 so that endoscopic portion 14 of surgical clip applier 10 can be introduced within body cavity 28. While MRI scanner 30 is scanning the surgical site 22, the user may treat tissue "T" (apply surgical clips) that is disposed within body cavity 28, without the clip applier 10 obstructing the view or distorting the image.

In some embodiments, all or a portion of surgical clip applier 10 or at least a part of endoscopic portion 14 and/or jaws 16 are constructed from non-ferrous metals to avoid any adverse imaging side effects during MRI scanning. Other suitable materials, for example, copolymers, plastics and/or carbon fiber, may also be utilized.

Additionally or alternatively, in other embodiments, all or a portion of surgical clip applier 10 or at least a part of endoscopic portion 14 and/or jaws 16 are constructed from a radio-translucent material to permit the penetration and passage of X-rays through endoscopic portion 14 (and/or jaws 16) of surgical clip applier 10. This allows a user (e.g., a radiologist) to view tissue that is behind endoscopic portion 14 and/or otherwise blocked h jaws 16 of surgical clip applies 10. For example, the components of this type of surgical instrument may be made of clear, translucent and/or radio-translucent plastic.

A detailed discussion of the construction and operation of the surgical clip applier and methods for its use are disclosed in commonly owned U.S. Pat. No. 7,637,917 entitled "ENDOSCOPIC SURGICAL CLIP APPLIER," the entire contents of which are incorporated herein by reference.

A detailed discussion of the construction and operation of the access port 24 and methods for its use during a surgical procedure, e.g., a natural orifice transluminal endoscopic surgery (NOTES) and a single incision surgical procedure, are disclosed in commonly owned U.S. Patent Publication No. 2009/0093752, entitled "SEAL ANCHOR FOR USE IN SURGICAL PROCEDURES," the entire contents of which are incorporated herein by reference.

Figure 2:
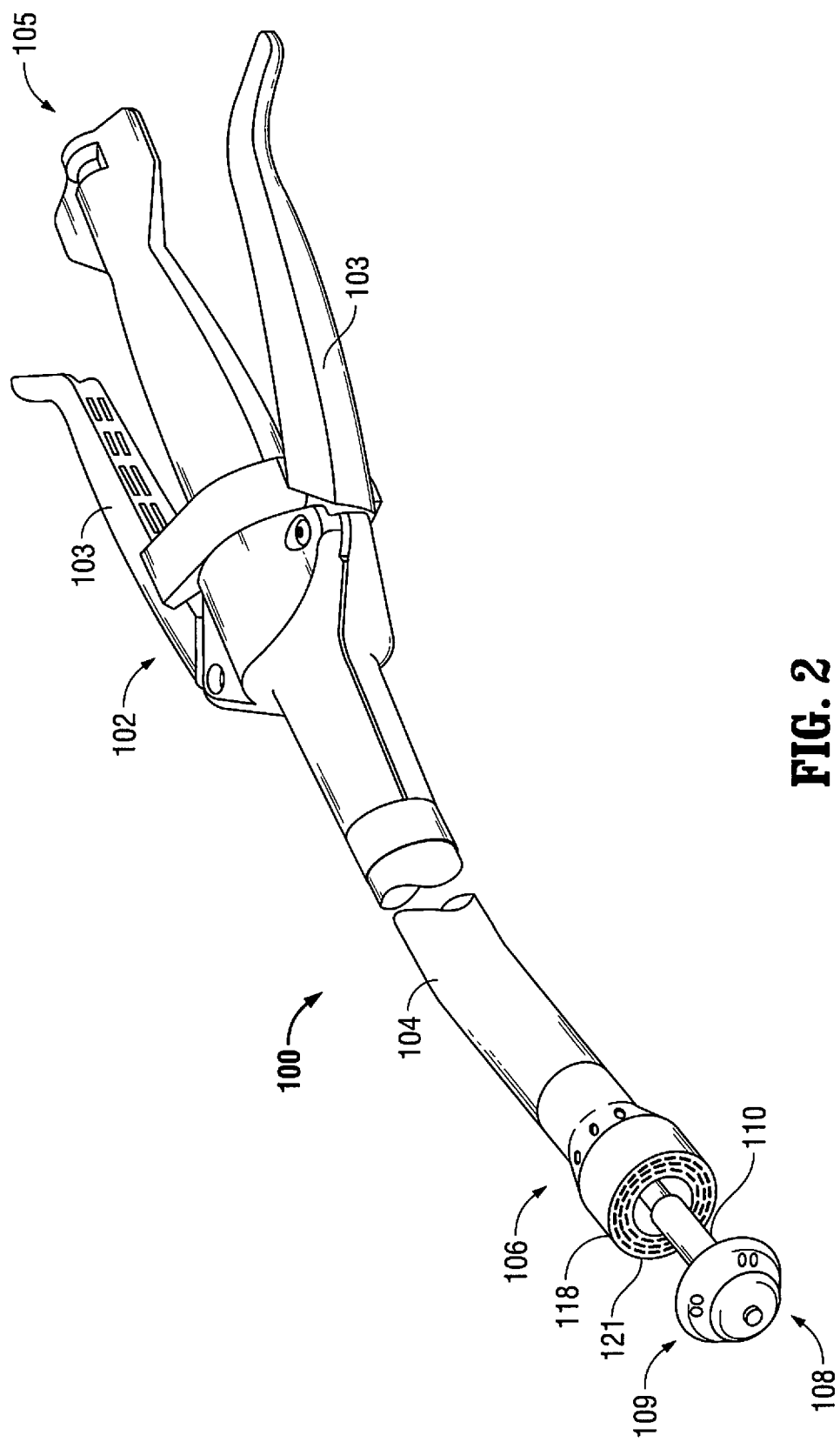
FIG. 2 is a perspective view of an exemplary surgical stapling device for performing a circular anastomosis including components being compatible with diagnostic scanning devices, in accordance with another embodiment of the present disclosure.

As seen in FIG. 2, a surgical instrument according to another embodiment of the present disclosure is in the form of a surgical stapling device 100 including a handle assembly 102 having one or more pivotable actuating handle members 103. Extending from handle assembly 102 is a tubular body portion 104 which may be constructed so as to have a curved shape along its length. Tubular body portion 104 terminates in a fastener ejection assembly 106 having a circular staple cartridge 118 including a tissue contacting surface 121 disposed at a distal end thereof. An anvil shaft 110 operatively couples an anvil assembly 108 to handle assembly 102. Anvil assembly 108 is repositionable from a location where it is spaced apart from staple cartridge 118 to a position where it is in close cooperative alignment (approximated) with staple cartridge 118. Anvil assembly 108 includes an anvil head 109. Surgical stapling device 100 further includes an advancing mechanism 105 that is configured to approximate or advance anvil head 109.

In operation, surgical stapling device 100 is positioned within a tubular organ in the body of the patient and the ends of the organ to be joined are positioned in a gap between staple cartridge 118 and anvil assembly 108. As is conventional, the ends of the organ may be secured around anvil shaft 110 by a purse string suture prior to approximation of anvil assembly 108 to staple cartridge 118. The anvil 108 and cartridge are then approximated to clamp the tissue and the surgical stapling device 100 is then fired to apply staples to the tissue by actuation of handle member 103.

In some embodiments, all or a portion of surgical stapling device 100 is constructed with non-ferrous metals to avoid any side effects, i.e. adverse affect on imaging, during MRI scanning. Other suitable materials, for example, copolymers, plastics and/or carbon fiber may also be utilized.

Additionally or alternatively, in other embodiments, all or a portion of surgical stapling device 100 is constructed with radio-translucent material to permit the penetration and passage of X-rays through the surgical instrument. For example, the components of this type of surgical instrument may be made of clear, translucent and/or radio-translucent plastic. These components can include the tubular body portion 104 and/or the end effector assembly (cartridge 118 and anvil assembly 108).

A detailed discussion of the construction and operation of the surgical stapling 100 device and methods for its use are disclosed in commonly owned U.S. Pat. No. 5,915,616, entitled "SURGICAL FASTENER APPLYING DEVICE," and U.S. Pat. No. 7,303,106 entitled "SURGICAL STAPLING DEVICE WITH VISUAL INDICATOR," the entire contents of which are incorporated herein by reference.

Figure 3:
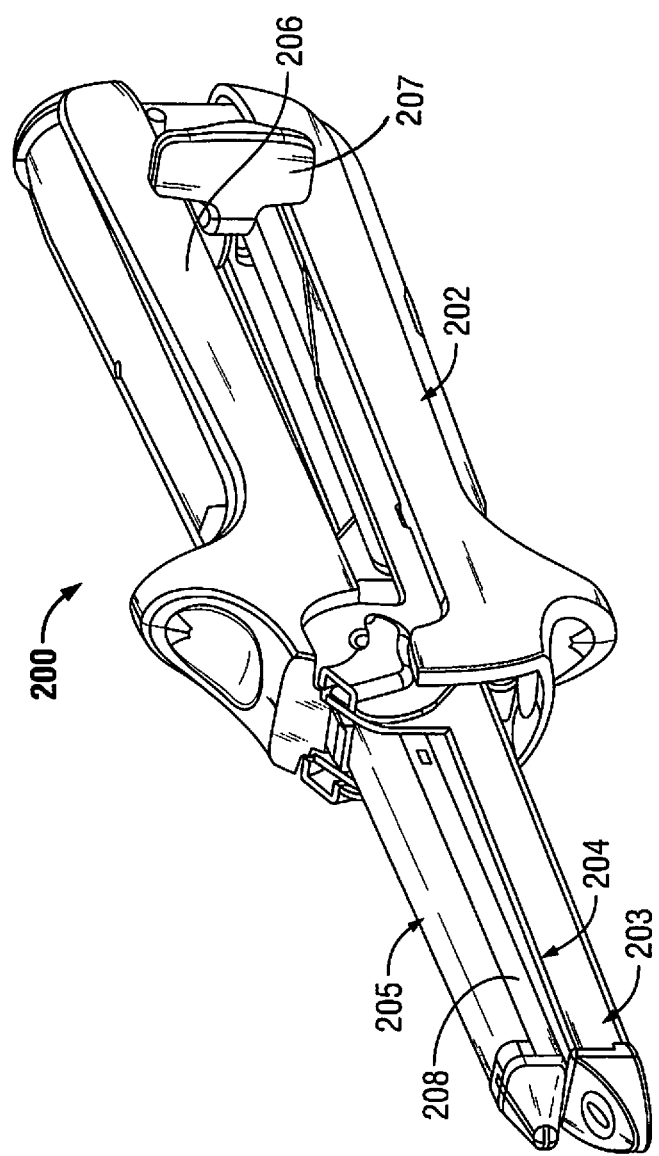
FIG. 3 is a perspective view of an exemplary surgical linear stapling device including components being compatible with diagnostic scanning devices, in accordance with yet another embodiment of the present disclosure.

Turning now to FIG. 3, a surgical stapling device for performing surgical anastomotic stapling, in accordance with another embodiment of the disclosure, is generally designated as 200. Surgical stapling device 200 includes a first handle 202 having a jaw 203 defining a staple cartridge receiving section extending from a distal end thereof, a staple cartridge 204 receivable in jaw 203, a second handle 206 having a jaw 205 defining an anvil section extending from a distal end thereof, and an anvil member 208 operatively associated with jaw 205. First and second handles 202, 206 are configured such that when clamped, staple cartridge 204 is substantially aligned with anvil member 208 such that these end effectors clamp tissue therebetween.

In operation, surgical stapling device 200 is fired similarly to and in accordance with other known surgical stapling devices. That is, firing knob 207 is actuated, i.e. advanced distally, to eject the staples from cartridge 204 into contact with anvil member 208. In some embodiments, all or a portion of surgical stapling device 200, and/or at least a portion of jaws 203, 205, is constructed with non-ferrous metals to avoid any adverse effects on imaging during MRI scanning. Other suitable materials, for example, copolymers, plastics and/or carbon fiber may also be utilized.

Additionally or alternatively, in other embodiments, all or a portion of surgical stapling device 200, and/or at least a portion of jaws 203, 205, is constructed with radio-translucent material to permit the penetration and passage of X-rays through the surgical instrument. For example, the components of this type of surgical instrument may be made of clear, translucent, and/or radio-translucent plastic.

A detailed discussion of the construction and operation of the surgical stapling device 200 and methods for its use are disclosed in commonly owned U.S. Pat. No. 6,202,914 entitled "SURGICAL STAPLER," and U.S. Pat. No. 7,055,730, entitled "SURGICAL FASTENER APPLYING APPARATUS," the entire contents of which are incorporated herein by reference.

Figure 4:
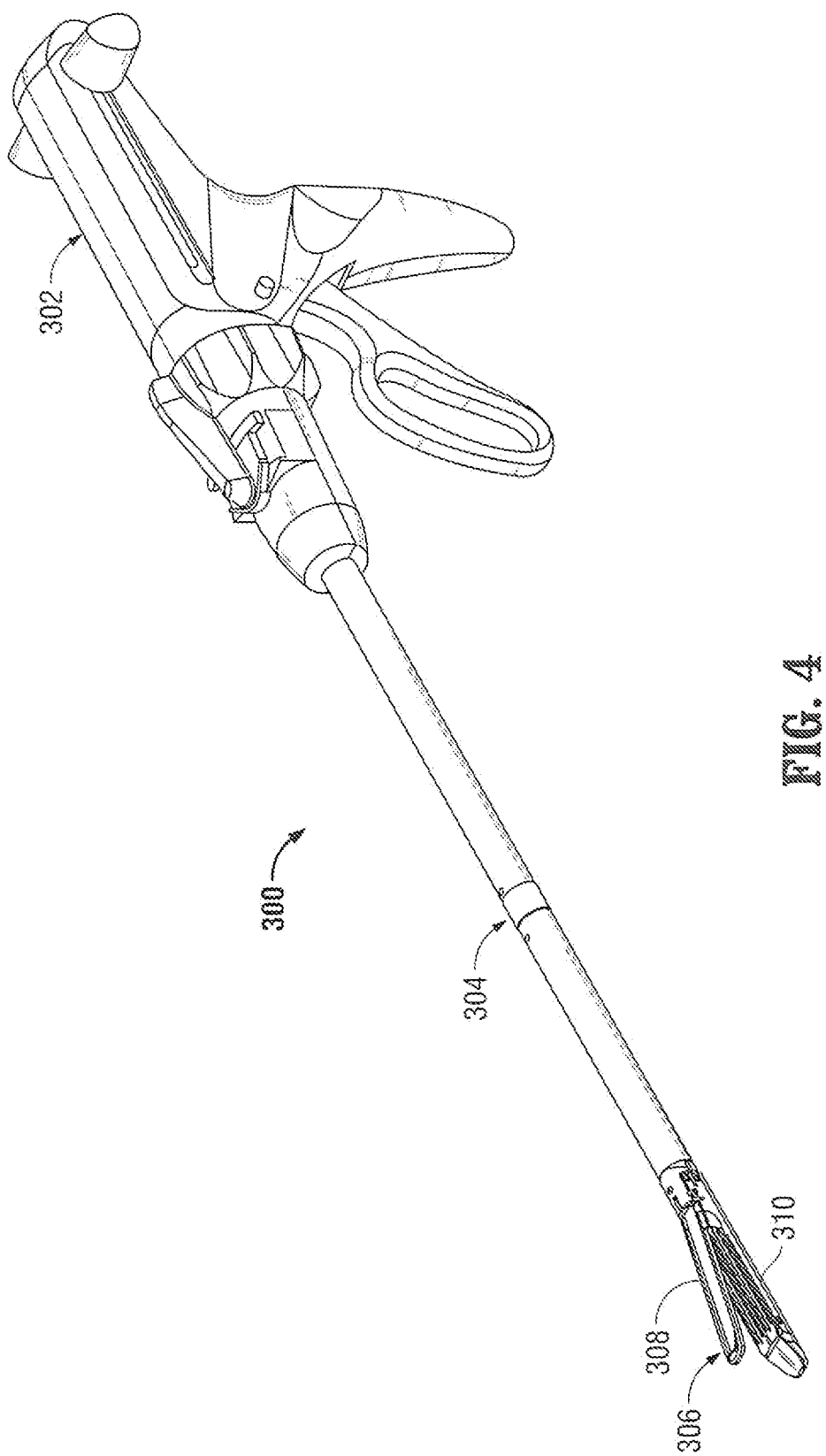
FIG. 4 is a perspective view of an exemplary endoscopic surgical linear stapling device including components being compatible with diagnostic scanning devices, in accordance with still yet another embodiment of the present disclosure.

Turning now to FIG. 4, a surgical stapling device of the laparoscopic type for performing surgical anastomotic stapling, in accordance with another embodiment of the disclosure, is generally designated as 300. Surgical stapling device 300 includes a handle 302, an end effector assembly 306, and an elongated shaft (endoscopic portion) 304 for interconnecting end effector assembly 306 to handle 302. End effector assembly 306 is designed to clamp and then to staple and divide tissue held therein. Accordingly, as seen in FIG. 4, end effector assembly 306 is a pair of opposed jaws including an anvil member 308 and a staple cartridge 310 pivotally coupled to one another. In operation, surgical stapling device 300 is fired similarly to and in accordance with other known surgical stapling devices as actuation of handle assembly 305 advances staples from cartridge 310.

In some embodiments, all or a portion of surgical stapling device 300 or at least a part of endoscopic portion 304 and/or jaws 308, 310 are constructed with non-ferrous metals to avoid any adverse effects on imaging during MRI scanning. Other suitable materials, for example, copolymers, plastics and/or carbon fiber may also be utilized.

Additionally or alternatively, in other embodiments, all or a portion of surgical stapling device 300, or at least a part of endoscopic portion 304 and/or end effector assembly 306 is constructed with radio-translucent material to permit the penetration and passage of X-rays through the surgical instrument. For example, the components of this type of surgical instrument may be made of clear, translucent, and/or radio-translucent plastic.

A detailed discussion of the construction and operation of surgical stapling device 300 and methods of its use are disclosed in commonly owned U.S. Pat. No. 5,865,361 entitled "SURGICAL STAPLING DEVICE," the entire contents of which are incorporated herein by reference.

Figure 5:
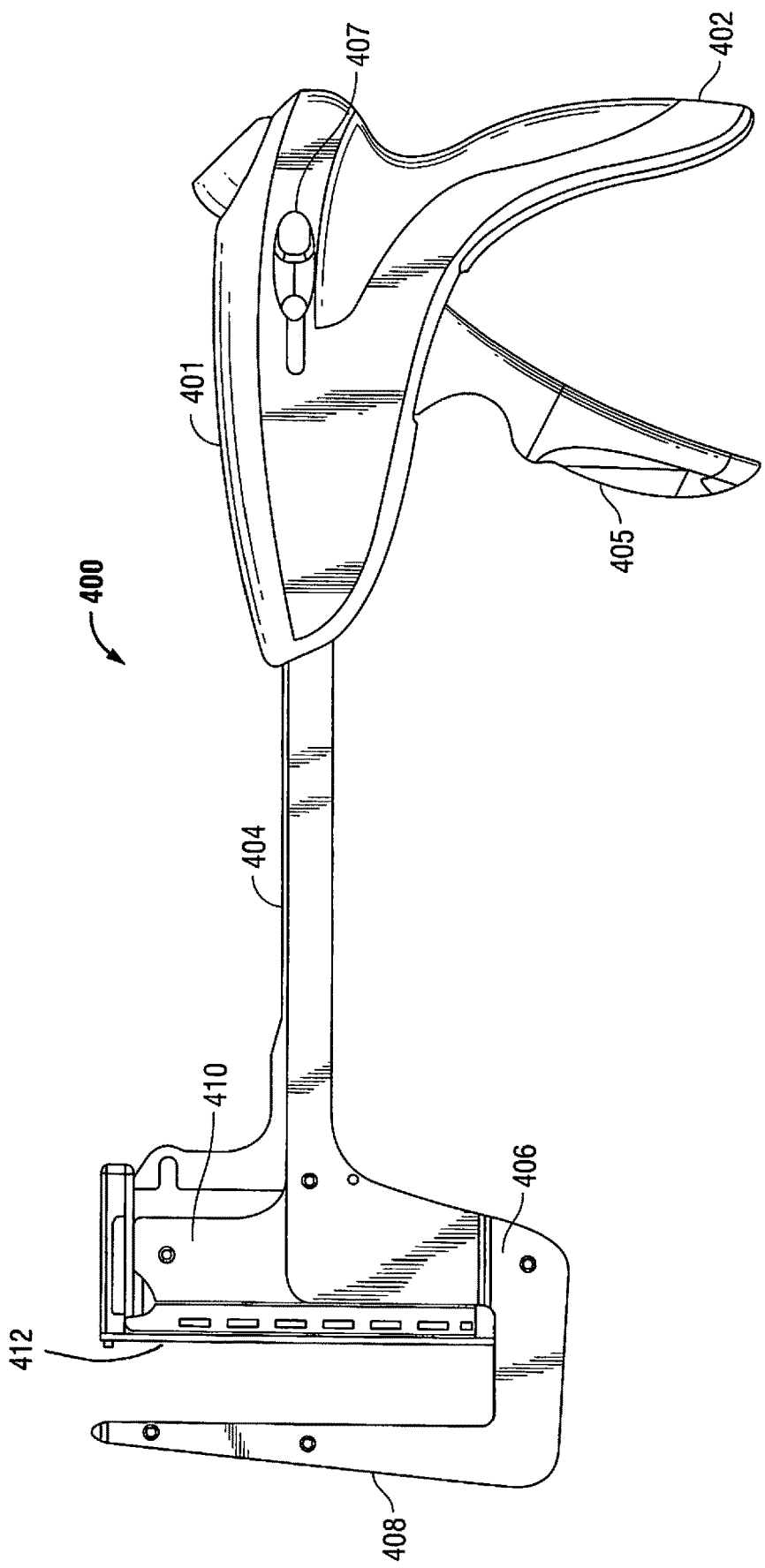
FIG. 5 is a perspective view of an exemplary surgical stapling device including components being compatible with diagnostic scanning device, in accordance with another embodiment of the present disclosure.

Turning now to FIG. 5, a surgical stapling device of the transverse anastomosis type for performing surgical anastomotic stapling, in accordance with yet another embodiment of the disclosure, is generally designated as 400. Surgical stapling device 400 includes a housing including a handle 402, an elongated member 404 extending from handle 402, a manual pin advancement mechanism 407, and an arm 406 extending from the distal end of member 404. Surgical stapling device 400 further includes an anvil member 408 orthogonally affixed to a distal end of arm 406 and a staple cartridge receiver 410 operatively coupled to the distal end of elongated member 404 for holding a disposable staple cartridge 412 thereon. In operation, the anvil assembly 408 and cartridge 412 are approximated to clamp tissue therebetween by advancement of cartridge 412. Handle 405 is then further actuated to advance the staples from cartridge 412 in a longitudinal direction, as surgical stapling device 400 is fired similarly to and in accordance with other known surgical stapling devices.

In some embodiments, all or a portion of surgical stapling device 400, and/or at least arm 406, is constructed with non-ferrous metals to avoid any side effects during MRI scanning. Other suitable materials, for example, copolymers, plastics and/or carbon fiber may also be utilized.

Additionally or alternatively, in other embodiments, all or a portion of surgical stapling device 400, and/or at least arm 406, is constructed with radio-translucent material to permit the penetration and passage of X-rays through the surgical instrument. For example, the components of this type of surgical instrument may be made of clear, translucent, and/or radio-translucent plastic.

A detailed discussion of the construction and operation of surgical stapling device 400 and methods of its use are disclosed in commonly owned U.S. Pat. No. 5,964,394 entitled "SURGICAL FASTENER APPLYING DEVICE," and U.S. Pat. No. 6,817,508, entitled "SURGICAL STAPLING DEVICE," the entire contents of which are incorporated herein by reference.

In alternate embodiments, the surgical instruments described herein can include a channel to deliver agents. That is, during an MRI, it may be advantageous to deliver MRI image enhancing agents directly from the instrument and into tissue that is being monitored within the operative space. Thus, the channel in these instruments would enable such delivery.

The surgical instruments disclosed herein can also have channels for delivery of therapeutic agents so the clinician can precisely deliver a drug or radiation treatment concurrent with surgical resection while under visualization. Such therapeutics can include for example imaging contrast agents and anti-cancer drugs for local tumor management post-resection.

It is also contemplated that instruments disclosed herein can be used in natural orifice translumenal endoscopic surgery (NOTES) applications. In some instances, these instruments can be used for example in the central airway/lung to resect tissue, e.g. for lung tumors, without the need opening the chest wall/thoracic cavity.

It should be understood that the foregoing description is only illustrative of the present disclosure. Various alternatives and modifications can be devised by those skilled in the art without departing from scope of the present disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques, e.g., single incision laparoscopic surgery (SILS®) and natural orifice translumenal endoscopic surgery (NOTES), are also intended to be within the scope of the disclosure.

What is claimed is:

1. A surgical instrument for treating tissue during use of a diagnostic scanning device, the surgical instrument comprising:
   a housing;
   an end effector assembly including first and second jaw members moveable relative to one another and a plurality of fasteners; and
   an actuating mechanism configured to eject the plurality of fasteners from the end effector assembly;
   wherein at least a portion of the end effector assembly is constructed from a material that is compatible with the diagnostic scanning device and that allows a user to insert and activate the end effector assembly to thereby treat tissue at a surgical site within a patient while the surgical site is monitored during diagnostic testing, wherein the entire end effector assembly is at least one of clear, transparent, translucent, and radio-translucent to the scanning device.

2. The surgical instrument according to claim 1, wherein the diagnostic scanning device is selected from the group consisting of magnetic resonance imaging, computed axial tomography scan, and x-ray.

3. The surgical instrument according to claim 1, wherein the compatible material is a non-ferrous metal.

4. The surgical instrument according to claim 1, wherein the compatible material is a non-metallic material such that at least a portion of the surgical instrument is radio-translucent during diagnostic testing.

5. The surgical instrument according to claim 1, wherein the actuating mechanism is a handle assembly, the handle assembly being operatively coupled to the end effector assembly, wherein actuation of the handle assembly operates the end effector assembly to treat tissue.

6. The surgical instrument according to claim 1, wherein the surgical instrument is a surgical stapling device.

7. The surgical instrument according to claim 6, wherein the end effector assembly includes a stapling cartridge disposed on the first jaw member and an anvil assembly disposed on the second jaw member, each being entirely composed of a material being compatible with the diagnostic scanning device to thereby staple tissue at the surgical site within the patient while the surgical site is monitored during diagnostic testing.

8. The surgical instrument according to claim 7, wherein the stapling cartridge and the anvil assembly are approximated towards each other to clamp tissue therebetween and to clinch the plurality of fasteners in tissue upon expulsion of the plurality of fasteners at the surgical site within a patient while the surgical site is monitored during diagnostic testing.

9. The surgical instrument according to claim 1, wherein the surgical instrument is a surgical clip applier.

10. The surgical instrument according to claim 9, wherein the clip applier further includes a handle portion, and a body extending distally from the handle portion and defining a longitudinal axis, wherein at least a portion of the body and the first and second jaw members are constructed from a material that is compatible with the diagnostic scanning device, wherein the clip applier is configured to apply each fastener of the plurality of fasteners to tissue at the surgical site within a patient while the surgical site is monitored during diagnostic testing.

11. The surgical instrument according to claim 1, wherein the end effector assembly is transparent to the scanning device.

12. The surgical instrument according to claim 1, wherein the end effector assembly is radio-translucent to the scanning device.

13. The surgical instrument according to claim 1, wherein the end effector assembly includes a body portion that supports the first and second jaw members.

14. A method of treating tissue during use of a diagnostic scanning device, the method comprising:
providing a surgical instrument including a housing, an end effector assembly having a plurality of fasteners, and an actuating mechanism configured to activate the end effector assembly, wherein at least a portion of the end effector assembly is constructed from a material that is compatible with the diagnostic scanning device and that allows a user to insert and activate the end effector assembly to thereby treat tissue at a surgical site within a patient while the surgical site is monitored during diagnostic testing, wherein the entire end effector assembly is at least one of clear, transparent, translucent, and radio-translucent to the scanning device;
inserting the end effector assembly into the surgical site;
scanning and monitoring the surgical site with the diagnostic scanning device; and
applying the plurality of fasteners to the tissue with the surgical instrument while scanning and monitoring the surgical site.

15. The method according to claim 14, wherein the surgical instrument is a surgical stapling instrument.

16. The method according to claim 14, wherein the surgical instrument is a surgical clip applier.

17. The method according to claim 14, wherein the end effector assembly includes a stapling cartridge and an anvil assembly, each being entirely composed of a material being compatible with the diagnostic scanning device to thereby staple tissue at the surgical site within a patient while the surgical site is monitored during diagnostic testing.

18. The method according to claim 14, wherein the diagnostic scanning device is selected from the group consisting of magnetic resonance imaging, computed axial tomography scan and x-ray.

19. The method according to claim 14, wherein the compatible material is a non-ferrous metal.

20. The method according to claim 14, wherein the compatible material is a non-metallic material.

* * * * *